US00PP36912P2

(12) United States Plant Patent
Dirr et al.

(10) Patent No.: US PP36,912 P2
(45) Date of Patent: Sep. 2, 2025

(54) ***DISTYLIUM* PLANT NAMED 'EH-60-22'**

(50) Latin Name: ***Distylium* spp.**
Varietal Denomination: EH-60-22

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/799,889

(22) Filed: Aug. 9, 2024

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226

CPC ... A01H 5/12; A01H 5/00; A01H 5/02; A01H 6/00

See application file for complete search history.

(56) References Cited

PUBLICATIONS

Dirr, Distylium: The Best New Plant You've Never Heard of, Grower Talks 2015, retrieved on Nov. 12, 2024, 4 pp. (Year: 2015).*
Vink, Flora Malesiana *Hamamelidaceae* 1957, ser. I 5 3, 363-370. (Year: 1957).*
Walker, A Revision of *Distylium* and Sycopsis (*Hamamelidaceae*) in Journal of the Arnold Arboretum 1944, 25:3, 319-341 (24 pp. total). (Year: 1944).*

* cited by examiner

*Primary Examiner* — June Hwu
(74) *Attorney, Agent, or Firm* — Cassandra Bright

(57) ABSTRACT

A new and distinct cultivar of *Distylium* plant named 'EH-60-22', characterized by its compact, layered (branches uniformly stacked) mounding habit; olive/reddish new foliage color and lustrous olive-green mature foliage. Plants have a low temperature tolerance within USDA Zones 6-9 and are tolerant of high temperatures to at least 95° F. The new variety is a *Distylium*, typically for ornamental garden use.

5 Drawing Sheets

Genus and species of plant claimed: *Distylium* spp.
Variety denomination: 'EH-60-22'.

BACKGROUND OF THE INVENTION

The present invention relates to a new and distinct cultivar of *Distylium* plant, botanically known as *Distylium* hybrid, a member of the Hamamelidaceae family, and hereinafter referred to by the cultivar name 'EH-60-22'.

'EH-60-22' originated as an open-pollinated seedling from seed collected from *Distylium* hybrid 'PIIDIST-I', U.S. Plant Pat. No. 24,410, growing in Watkinsville, Georgia. 'EH-60-22' is a *Distylium* spp. hybrid (*Distylium myricoides* x *D. racemosum*) selected in 2022 by the inventors in a cultivated environment in Watkinsville, GA.

Asexual reproduction of 'EH-60-22' by stem cuttings since 2022 has shown that all the unique features of 'EH-60-22', as herein described, are stable and reproduced true-to-type through successive generations of such asexual propagation. First propagation took place at a research nursery in Watkinsville, Georgia.

SUMMARY OF THE INVENTION

'EH-60-22' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'EH-60-22' from all other varieties in commerce known to the inventor:

1. Compact, layered (branches uniformly stacked), and mounding growth habit.
2. Very low-growing, almost groundcover-like.
3. Olive/reddish new growth.
3. Small, strapped-shaped leaves, lustrous olive-green foliage on mature growth.
4. Temperature tolerance within USDA Zones 6-9.

PARENTAL COMPARISON

Plants of the new cultivar 'EH-60-22' are comparable to the seed parent in most horticultural characteristics. However, the new variety 'EH-60-22' differs in the following:

1. Plant habit of 'EH-60-22' is compact, layered, and mounding, while the plant habit of the parent is upright and rounded.

COMMERCIAL COMPARISON

Plants of the new cultivar 'EH-60-22' can be compared to the commercial cultivar 'PIIDIST-IV', U.S. Plant Pat. No. 25,984, in most horticultural characteristics. However, the new variety 'EH-60-22' differs in the following:

1. Plants of 'EH-60-22' are much shorter than plants of this comparator.

2. Mature growth of 'EH-60-22' olive-green, whereas the mature growth of this comparator is blue-green.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Distylium*.

DETAILED BOTANICAL DESCRIPTION

Figure 1:
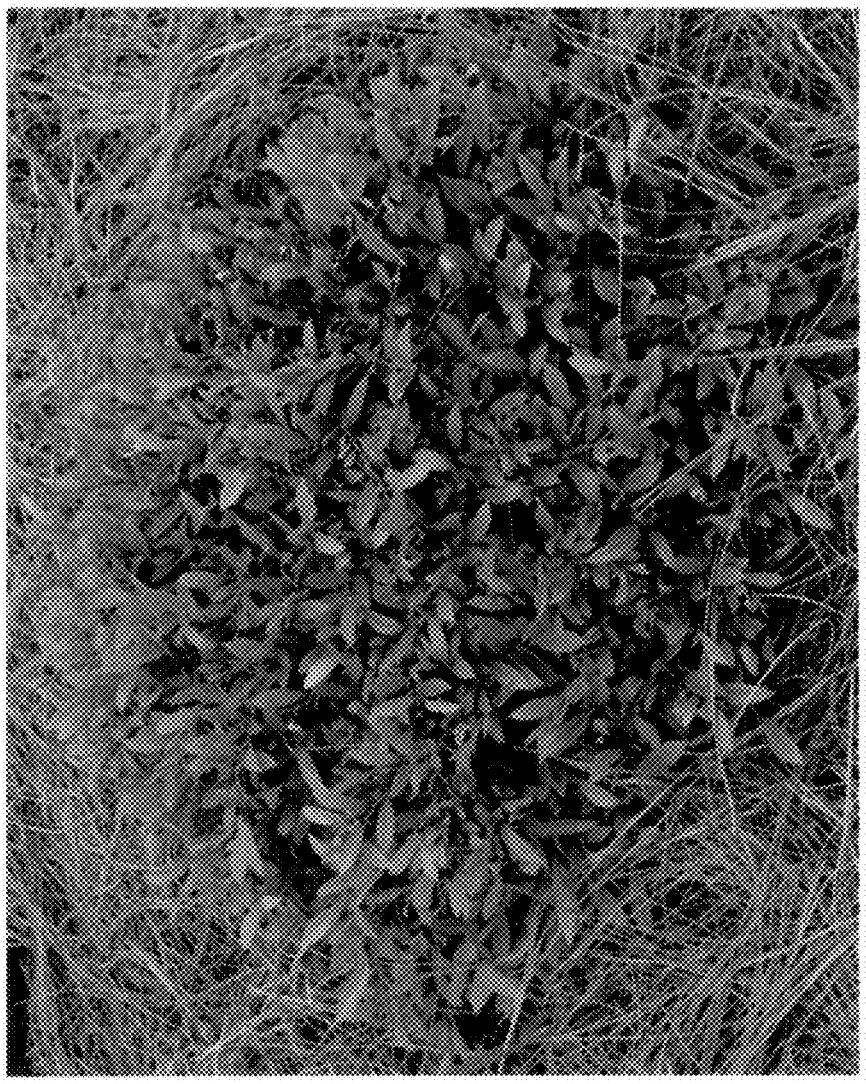
FIG. 1 illustrates the overall appearance and growth habit of a two-year-old 'EH-60-22' plant in the ground.
Figure 2:
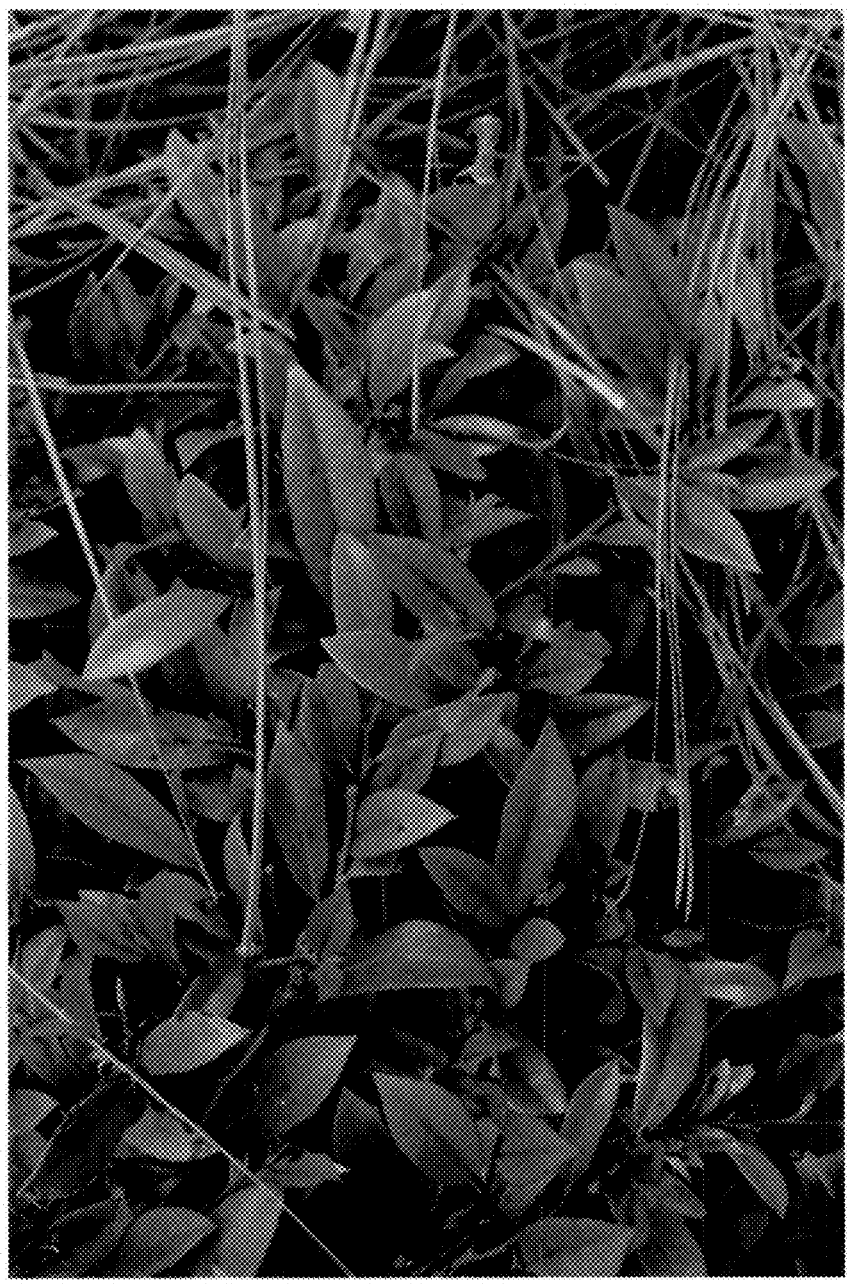
FIG. 2 illustrates a close-up of the new growth of a two-year-old 'EH-60-22' plant in the ground.
Figure 3:
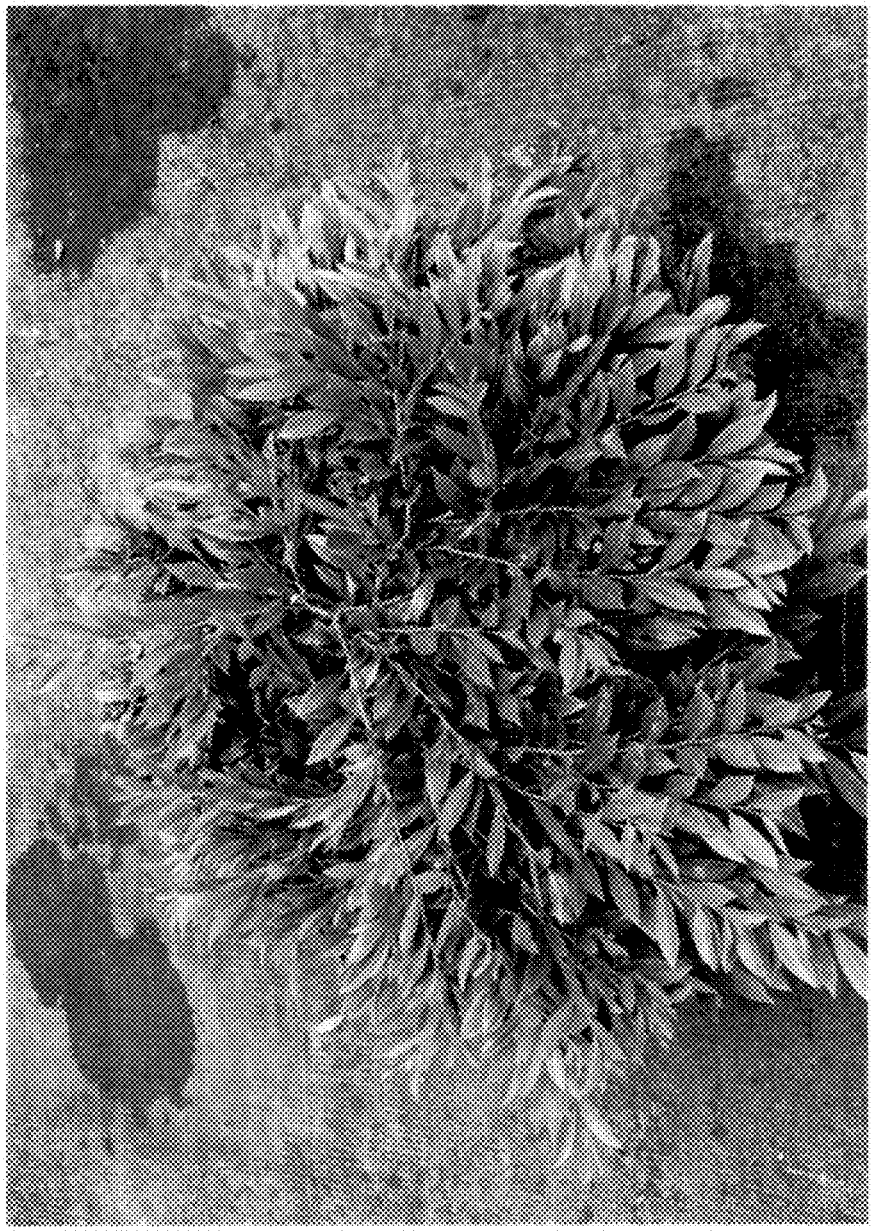
FIG. 3 illustrates a two-year-old 'EH-60-22' in a container.
Figure 4:
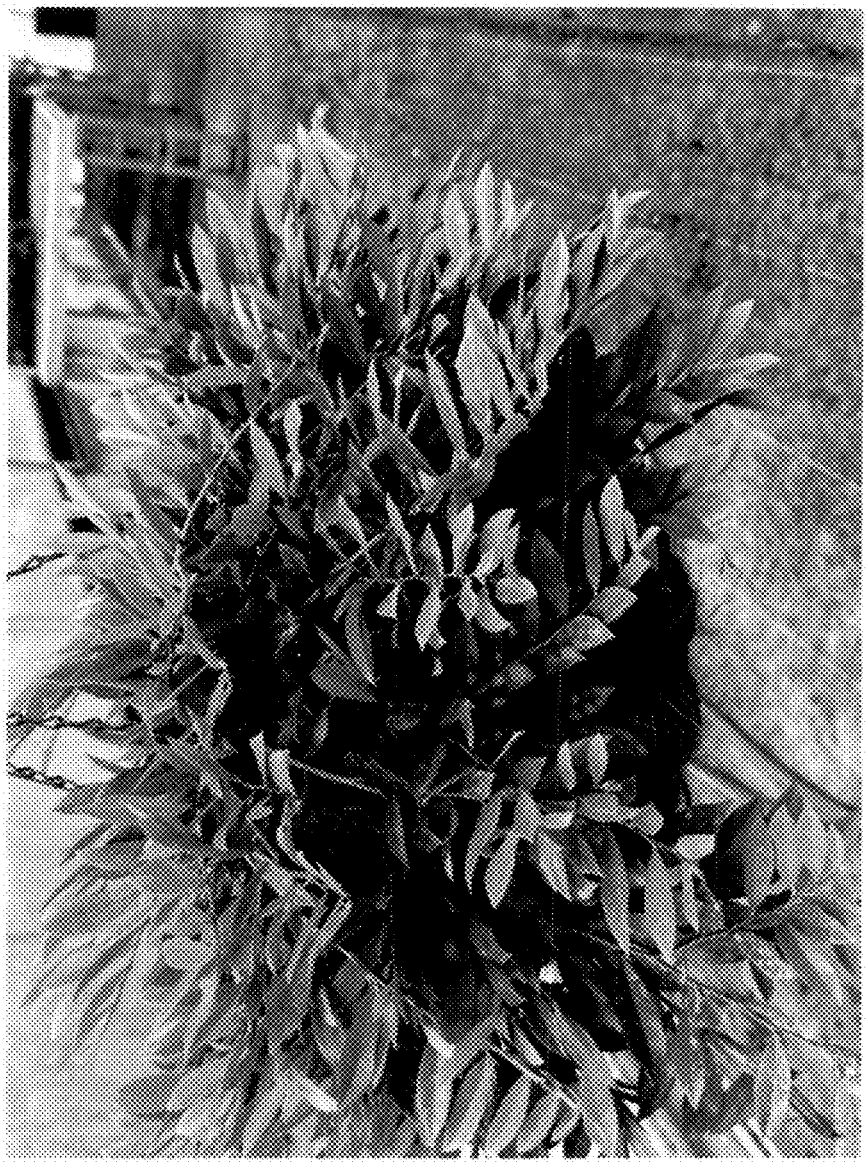
FIG. 4 illustrates a two-year-old 'EH-60-22' in a hanging basket.
Figure 5:
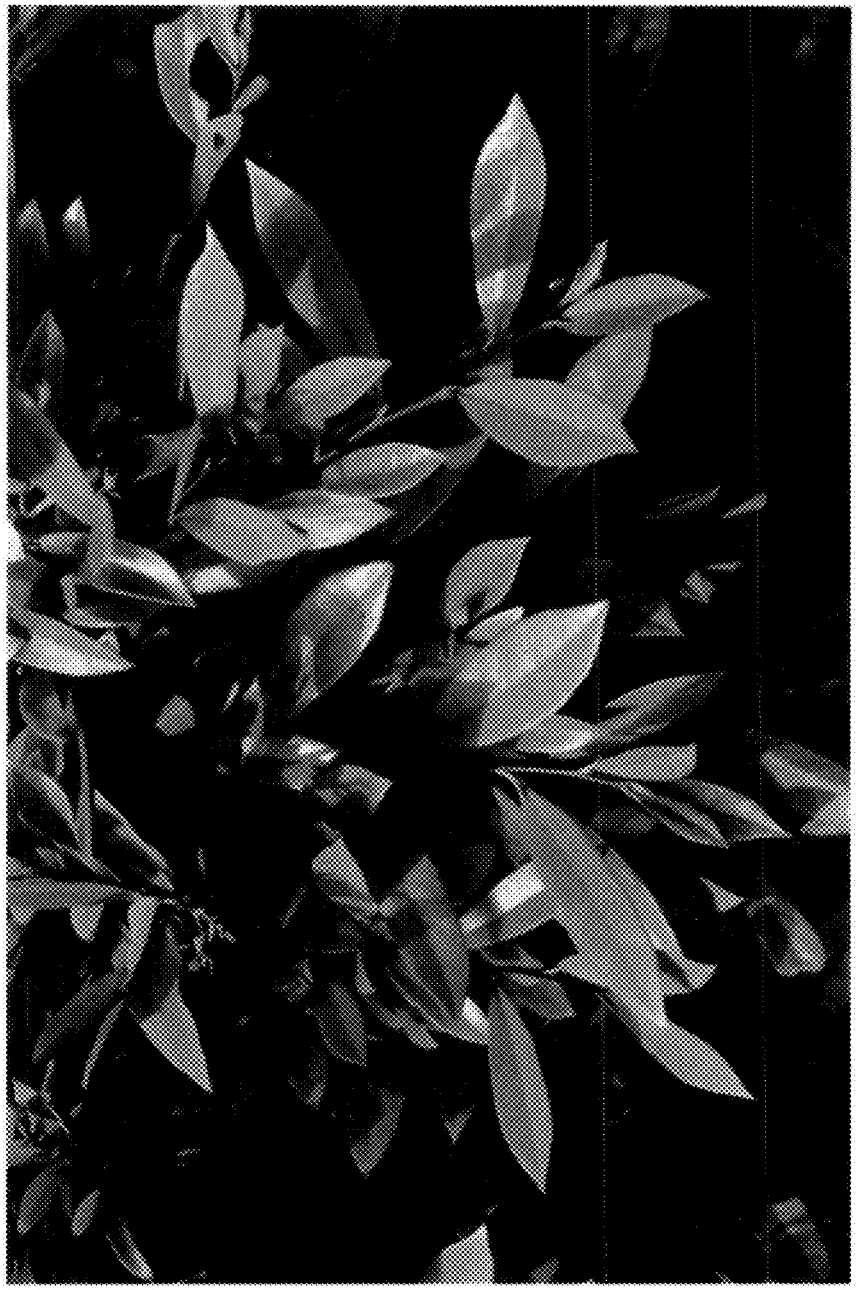
FIG. 5 illustrates a two-year-old 'EH-60-22' close up of the foliage.

In the following description, color references are made to The Royal Horticultural Society Colour Chart, 2015 Edition, except where general terms of ordinary dictionary significance are used. Plants for the description were grown in a 23.03-liter container under outdoor conditions in Watkinsville, GA. Plants were about two years old when the description was recorded.

Botanical classification: *Distylium* 'EH-60-22'.

PROPAGATION

Type of propagation typically used: Vegetative stem cuttings.

Time to initiate roots: About 6 weeks at 32° C. in summer.

Number of days to produce a rooted plant: About 3 months at 32° C. in summer.

Root description: Medium, well-branched, diffuse, and extensive. Colored RHS Greyed-White 156A.

PLANT

Type of plant: Broadleaf evergreen shrub.

Age of plant described: 2 years old.

Container size of the plant described: 26.49 liters.

Growth habit: Multi-stemmed, compact, mounded, spreading. Freely branching; removal of the terminal bud enhances lateral branch development.

Height: About 20.3 cm.

Plant spread: About 73.66 cm.

First year stems:
- *Length*.—About 15 cm.
- *Diameter*.—About 2.5 mm.
- *Shape*.—Round.
- *Color*.—RHS Yellow-Green 144A.
- *Pubescence*.—Fine.
- *Strength*.—Flexible.
- *Lenticels*.—Diameter: About 1 mm. Color: RHS Greyed-Green 197B.

Second year stems:
- *Length*.—35 cm.
- *Diameter*.—3 mm or more.
- *Shape*.—Round.
- *Color*.—RHS Brown N200A.
- *Pubescence*.—None.
- *Strength*.—Flexible when young; less when mature.

Trunk/main stem diameter: About 1 cm at the soil line.

Trunk/main stem color: RHS Greyed-Green 197C.

Bark: Does not exfoliate, covered with abundant lenticels, RHS Brown N199C in color, about 1 mm in diameter.

Internode length: About 1 cm.

Vegetative buds:
- *Arrangement*.—Alternate.
- *Shape*.—Ovoid with fused, pubescent bud scales.
- *Length*.—About 3 mm.
- *Width*.—About 1 mm.
- *Color*.—RHS Brown N199B.

FOLIAGE

Leaf:
- *Arrangement*.—Alternate, simple.
- *Average length*.—About 5.5 cm.
- *Average width*.—About 1.5 cm.
- *Shape of blade*.—Ovate-lanceolate.
- *Apex*.—Acute.
- *Base*.—Cuneate.
- *Margin*.—Entire, occasionally undulating.
- *Texture of top surface*.—Smooth, thick, leathery.
- *Texture of bottom surface*.—Smooth, thick, leathery.
- *Color*.—Young foliage upper side: RHS Yellow-Green 152A mixed with Greyed-Red 178A along the midvein and margin. Young foliage under side: RHS Yellow-Green 152B. Fully expanded foliage upper side: RHS Yellow-Green 147A. Fully expanded foliage under side: RHS Yellow-Green 146B.
- *Venation*.—Type: Pinnate. Color, upper side, midrib: RHS Yellow-Green 144C. Color, under side, midrib: RHS Yellow-Green 144C. Color, secondary: RHS Yellow-Green 146A.
- *Petiole*.—Length: About 4 mm. Diameter: About 1 mm. Color: RHS Yellow-Green 144A, both surfaces. Pubescence: Fine, RHS Yellow-Green 144A in color.

FLOWER

Natural flowering season: Late winter, approximately January to February in Watkinsville, GA. Individual flowers are showy for approximately 1 week and are self-cleaning.

Flower type and habit: Apetalous flowers with pubescent, 5-parted calyx are borne on short racemes from the leaf axils.

Inflorescence type: Raceme.

Inflorescence size: 2.5 cm in height and 3.75 cm in diameter.

Inflorescences per lateral branch: 15 to 21.

Flowers per inflorescence: 5 to 9 flowers per inflorescence.

Flower diameter: About 3 mm.

Flower height: About 5 mm.

Persistence: Self-Cleaning.

Fragrance: None.

Pedicels:
- *Length*.—About 2 mm.
- *Color*.—RHS Yellow-Green 146C with pubescence colored Greyed-Orange 165A.

Peduncles:
- *Length*.—About 1.2 cm.
- *Color*.—RHS Yellow-Green 146C with pubescence colored Greyed-Orange 165A.

Calyx: Diameter: 3 mm. Height: 2 mm. 5 sepals radially arranged, about 2 mm long and 1 mm wide colored Yellow-Green 146C upper and lower surfaces. Sepal shape oblong. Sepal apex acute, sepal base truncate. Sepal texture glabrous all surfaces.

REPRODUCTIVE ORGANS

Stamens:

*Number*.—7 to 10.

*Filament length*.—About 3 mm.

*Filament width*.—Less than 1 mm.

*Color*.—RHS Greyed-Purple 185A.

*Pollen*.—Amount: Moderate. Color: RHS Yellow-White 158D.

Pistil:

*Position*.—Superior.

*Length*.—Approximately 1.1 mm.

*Width*.—2 mm.

*Color*.—RHS Yellow-Green 146B.

*Style*.—Number: 2 per flower. Length: 3 mm. Color: RHS Yellow-Green 146B.

*Stigma*.—Number: 2 per pistil. Length: About 6 mm. Color: RHS Greyed-Red 178B. Ovary: Number: 2 per flower. Length: About 3 mm. Width: About 2 mm. Color: RHS Yellow-Green 146B.

OTHER CHARACTERISTICS

Temperature tolerance: Low temperature tolerance within USDA Zones 6-9. High temperature tolerance of at least 95 degrees F.

Fruits and seeds: Not observed to date.

Disease/pest resistance: Disease and pest resistance: Not observed to be susceptible nor resistant to normal disease and pest of *Distylium*.

What is claimed is:

1. A new and distinct cultivar of *Distylium* plant named 'EH-60-22', substantially as illustrated and described herein.

* * * * *